United States Patent
Paranjpe et al.

[11] Patent Number: 5,760,573
[45] Date of Patent: Jun. 2, 1998

[54] PLASMA DENSITY MONITOR AND METHOD

[75] Inventors: Ajit Pramod Paranjpe, Dallas; Steve Show-Wu Huang, Richardson, both of Tex.

[73] Assignee: Texas Instruments Incorporated, Dallas, Tex.

[21] Appl. No.: 485,203

[22] Filed: Jun. 7, 1995

Related U.S. Application Data

[62] Division of Ser. No. 305,493, Sep. 12, 1994, abandoned, which is a continuation of Ser. No. 154,377, Nov. 18, 1993, abandoned.

[51] Int. Cl.⁶ ............................. G10N 27/00; G01R 33/00
[52] U.S. Cl. ........................ 324/71.1; 324/239; 324/464
[58] Field of Search ........................... 324/71.1, 654, 324/655, 204, 239, 71.3; 331/35

[56] References Cited

U.S. PATENT DOCUMENTS

| | | | |
|---|---|---|---|
| 3,665,298 | 5/1972 | Geiger | 324/239 |
| 4,560,929 | 12/1985 | Melnyk | 331/65 |
| 4,595,877 | 6/1986 | Dülk | 324/239 |
| 4,859,942 | 8/1989 | Charton et al. | 324/645 |
| 5,135,604 | 8/1992 | Kumar et al. | 216/59 |
| 5,198,764 | 3/1993 | Spencer | 331/65 |
| 5,315,243 | 5/1994 | Kempster et al. | 324/204 |
| 5,359,282 | 10/1994 | Teii et al. | 324/71.1 |
| 5,365,147 | 11/1994 | Shinohara et al. | 315/111.21 |

Primary Examiner—Ernest F. Karlsen
Attorney, Agent, or Firm—Warren L. Franz; Wade James Brady, III; Richard L. Donaldson

[57] ABSTRACT

A plasma density monitor is described for determining the ion current of a plasma flowing through a conduit (14). The monitor comprises a plate (18) having a face and an orifice extending from the face through the plate. The internal surface of the orifice conforms with the internal surface of the conduit when the face is adjacent the conduit. The monitor also comprises a detector circuit (22) for sensing the ion current collected by the internal surface of the plate (18). Another embodiment monitors plasma density by determining electrical conductivity in the afterglow of a microwave induced plasma. A resonant LC circuit (50, C3) has a multi-turn coil (C3) surrounding the conduit, an RF oscillator circuit (54, 56) for driving the LC circuit, and a circuit (64, 66, 68, 70, 72, 76) for measuring the decay time of the LC circuit. Plasma flowing through the conduit alters the resistivity of the coil and the time constant of the LC circuit proportional to the electrical conductivity of the flowing plasma.

20 Claims, 2 Drawing Sheets

PLASMA DENSITY MONITOR AND METHOD

This is a Division, of application Ser. No. 08/305,493 filed on Sep. 12, 1994, now abandoned; which is a Continuation of Ser. No. 08/154,377 filed Nov. 18, 1993 now abandoned.

TECHNICAL FIELD OF THE INVENTION

This invention relates in general to electronic measurement devices and more particularly to a plasma density monitor and method.

BACKGROUND OF THE INVENTION

Plasma density (the electron and ion concentrations of a plasma) is a key parameter that determines the performance of plasma processes for integrated circuit fabrication. Electrons are responsible for initiating gas phase chemistry, while ions activate surface chemistry. Several plasma processes use a combination of radio frequency ("RF") and microwave sustained plasmas. The plasma density achieved in such a mixed mode of operation is considerably enhanced. While RF generated plasmas are quite stable and repeatable from run to run, plasmas generated by remote microwave plasma sources may exhibit considerable variation in properties. This variation is caused by the non-linear characteristics of the microwave applicator and associated tuning elements. Frequently, the position of the tuning elements for igniting the plasma differs considerably from the position used during steady-state operation. Since the tuning process is not automated, variations from run to run occur. The detrimental effects of these problems can be mitigated through feedback control of microwave power to maintain a constant plasma density. One necessary component of such a feedback system is a probe for monitoring the plasma density.

Langmuir probes have been commonly used for measuring the electron number density in plasma discharges. Conceptually, Langmuir probe measurements are the simplest way of determining the electron number density of a plasma. Langmuir probes are generally manufactured from small diameter (5 millimeter) conductive wires. The wire is electrically insulated except for a short portion at one end of the probe. The exposed portion of wire is inserted into the plasma for measurement. A plasma will strike the exposed portion of the wire and generate a small current. The current can be detected and can be empirically related to a known plasma strength.

The practical implementation of a Langmuir probe is difficult. Langmuir probes are intrusive, susceptible to RF interference in discharges powered by RF sources, and are accurate only within a factor of two. Part of the imprecision is due to experimental limitations such as arcing, deposits forming on the probe, secondary emissions from the probe and etching of the probe. Actual probe operations can deviate from ideal probe theory thereby complicating interpretation of results. Also, operation of a Langmuir probe may interfere with integrated circuit manufacturing processes. Langmuir probes are generally ill-suited for measuring weak plasma densities. The ion current produced by a weak plasma and sensed by a Langmuir probe is extremely low and is difficult to discern from background noise. This is due, at least in part, to the small surface area of the exposed portion of a Langmuir probe. The active area of the probe cannot be increased without also increasing the problems described above. For these reasons, Langmuir probes are rarely used for routine measurements.

Therefore, a need has arisen for a plasma density probe which is accurate, which is suitable for use with weak plasmas, which is durable, and which does not interfere with integrated circuit manufacturing processes.

SUMMARY OF THE INVENTION

In accordance with the present invention, a plasma density monitor and method are provided which substantially eliminate or reduce disadvantages and problems associated with prior plasma density monitors.

A plasma density monitor is described for determining the ion current of a plasma flowing through a conduit. The monitor comprises a plate having a face and an orifice extending from the face through the plate. The internal surface of the orifice conforms with the internal surface of the conduit when the face is adjacent the conduit. The monitor also comprises a detector circuit for sensing the ion current collected by the internal surface of the plate.

A first technical advantage of the disclosed device is its precision. Experimental results have demonstrated that the output of the probe does not vary significantly between identical test conditions.

A second technical advantage of the disclosed device is its sensitivity. The geometry of the probe allows the monitor to measure weak plasma densities generated by microwave sources, RF sources and mixed mode sources.

A third technical advantage of the disclosed device is its non-invasive nature. The inside surface of the probe collects a small portion of the plasma ion current without perturbing the flow of the plasma through the plasma delivery tube. This allows the probe to be used during wafer manufacture without affecting the resultant wafer.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

The preferred embodiment of the present invention and its advantages are best understood by referring to FIGS. 1 through 5 of the drawings, like numerals being used for like and corresponding parts of the various drawings.

ION CURRENT MONITOR

At typical operating pressures of an integrated circuit manufacturing process (50–1000 mTorr), a plasma sheath surrounding a probe is weakly-collisional.

If the plasma is assumed to be collision-dominated, the ion current collected by a probe is given by $$I_0 = A_p \left( \frac{9\epsilon_0 \mu_i}{8} \right) \left( \frac{V_0^2}{l_{sh}^3} \right) \quad (1)$$

where $\mu_i$ is the ion mobility, $\beta_0$ is the permittivity of free space, $1_{sh}$ is the sheath thickness, and $A_p$ is the surface area of the probe. This may also be expressed in terms of the ion number density ($n_i$) at a point a quarter way into the plasma sheath.

$$I_0 = 0.6 A_p \left[ \frac{n_i^3 e^3 \mu_i^2 V_0}{\epsilon_0} \right]^{1/2} \quad (2)$$

where e is the charge of an electron. The time-averaged voltage is assumed to be equal to the probe voltage, since the plasma potential of an afterglow plasma is very close to ground potential.

The corresponding expression for a collisionless sheath is $$I_0 = A_p \left( \frac{4\epsilon_0}{9} \right) \left( \frac{2e}{m_i} \right)^{1/2} \left( \frac{V_0^{3/2}}{l_{sh}^2} \right) \quad (3)$$

or equivalently $$I_0 = 0.4 A_p e n_i \left( \frac{2eV_0}{m_i} \right)^{1/2}$$

where $m_i$ is the mass of the ion.

In both cases, the ion current collected by the probe is dependent on the ion number density. While the exact ion number density cannot be calculated because the sheath dynamics are intermediate between being collision-dominated and collisionless, the ion current collected by the probe may be used as a relative measure of the ion number density. This has been shown to be adequate for the purpose of feedback control of microwave power in plasma processes.

Figure 1:
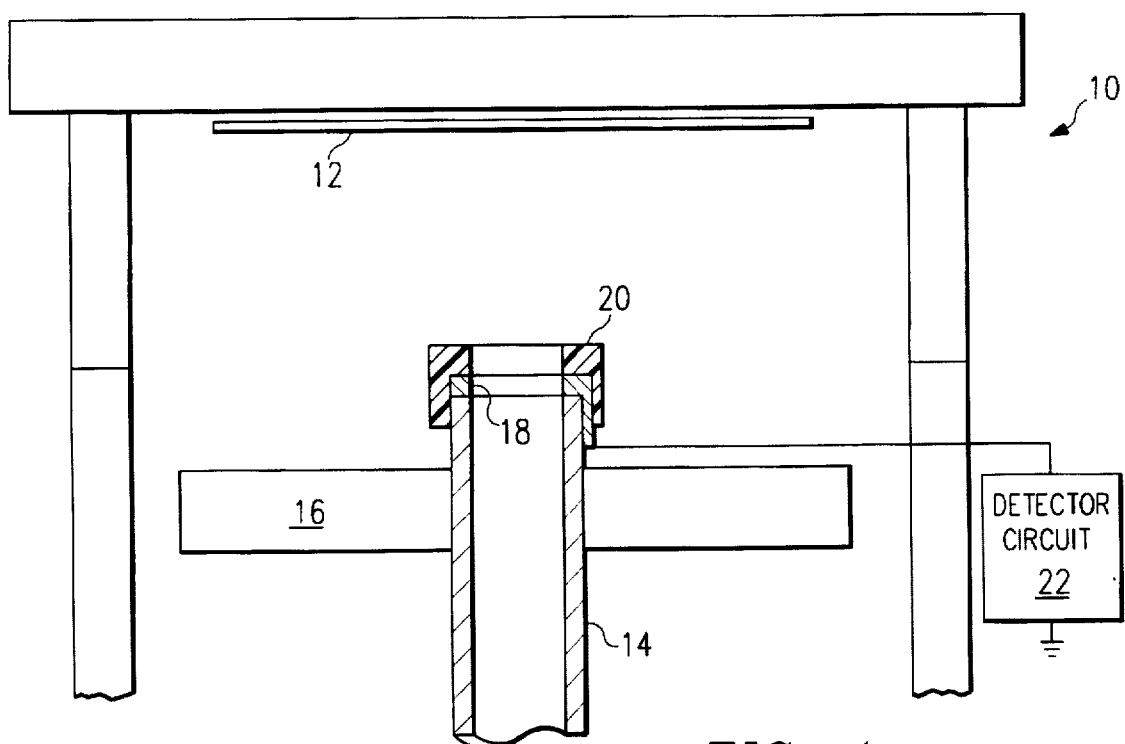
FIG. 1 depicts a partially cross-sectional, partially block diagram of a microwave processing chamber.

FIG. 1 depicts a partially cross-sectional, partially block diagram of a microwave processing chamber indicated generally at 10. As is known in the art, chamber 10 is used in semiconductor manufacturing processes to expose a semiconductor wafer 12 to plasmas induced by microwaves, RF waves or both. The plasmas may be used to alternately etch or deposit layers on wafer 12. In the depicted chamber 10, a remote microwave afterglow plasma is generated outside the chamber and, together with chemical reactants is conveyed to wafer 12 through a conduit 14. Conduit 14 is manufactured from a non-conductive material such as quartz or a suitable ceramic. A counter electrode 16 surrounds conduit 14. A planar probe 18 is integrated into conduit 14 and is retained by a threaded cap 20.

Probe 18 samples the plasma density of plasma in conduit 14 by collecting a small portion of the ions present in the plasma. In the depicted embodiment, probe 18 is a plate having a cylindrical passageway placed at the exit end of conduit 14. The passageway of probe 18 has the same diameter as, or "conforms" to, the inside diameter of conduit 14. Probe 18 and cap 20 are more fully described in connection with FIG. 2.

Probe 18 is electrically connected to a sensing circuit 22 for generating a signal representative of the ion current collected by probe 18. Circuit 22 is more fully described in connection with FIG. 3.

Figure 2:
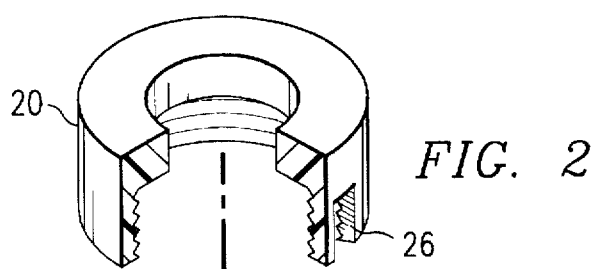
FIG. 2 depicts an isometric view of the disclosed ion current probe.

FIG. 2 depicts an isometric view of the disclosed ion current probe 18. Conduit 14 is typically a 1 in quartz tube. It is threaded near its end, indicated by the parallel arced lines, to receive cap 20 in an interlocking manner. Probe 18 has a lead 24 attached thereto to facilitate connection to sensing circuit 22 (depicted in FIGS. 1 and 3). In the depicted embodiment, probe 18 is a ring having an inside diameter of 1 in and a thickness or height of ⅛ in. Probe 18 is manufactured from a relatively inert metal such as nickel, platinum, chromium, molybdenum and combinations thereof. Cap 20 has a complementary set of grooves on an inner wall to receive the end of conduit 14 in an interlocking manner and has a notch 26 to receive lead 24. Cap 20 is manufactured from a chemically non-reactive material such as Teflon. Cap 20 may be omitted from the plasma density monitor if other means are provided for securing probe 18 against the flow of plasma through conduit 14. Also, the exposed conducting surface of probe 18 should not vary depending upon the method of securing probe 18 to conduit 14.

As depicted, the inside diameter of conduit 14, the inside diameter of probe 18 and the smallest inside diameter of cap 20 are equal in size to minimize any disturbance to the plasma flowing through conduit 14. Although the disclosed invention is described in connection with a conduit having a cylindrical passageway, the probe may be adapted for use with other conduit geometries.

Figure 3:
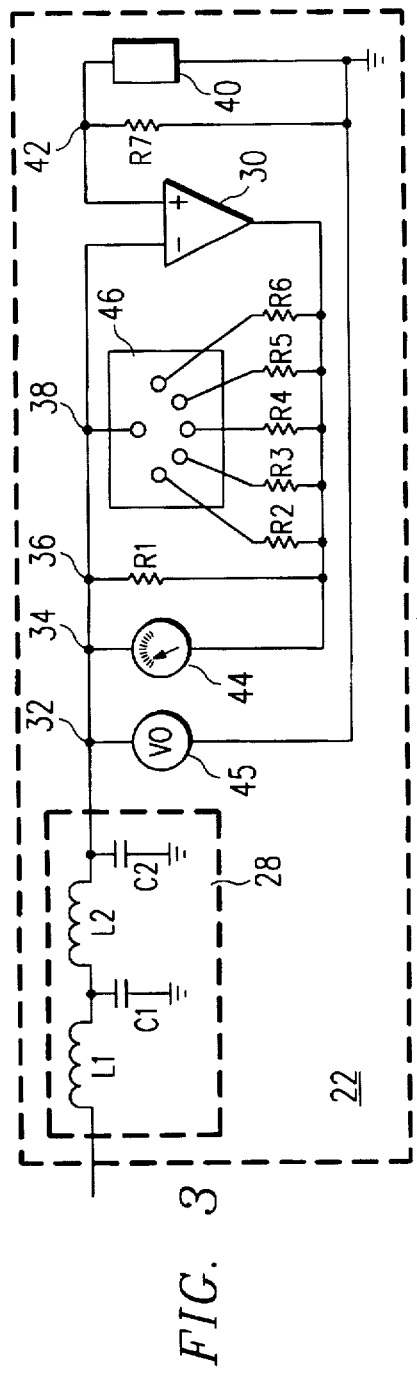
FIG. 3 depicts a partially schematic, partially block diagram of the circuit depicted in FIG. 1.

FIG. 3 depicts a partially schematic, partially block diagram of the circuit 22 depicted in FIG. 1. Circuit 22 comprises an RF filter 28 connected to the inverting input of an op-amp 30 through nodes 32, 34, 36 and 38. The first terminal of a reference voltage source 40 is connected to the non-inverting input of op-amp 30 through node 42. The second terminal of reference voltage source 40 is connected to ground. The output of op-amp 30 is connected to node 34 through a volt meter 44. A second reference voltage source 45 connects node 32 to ground. A resistor R1 connects node 36 to the output of op-amp 30. A switch 46 alternatively connects one of a group of resistors R2 through R6 to node 38 and to the output of op-amp 30. A resistor R7 connects node 42 to ground.

RF filter 28 comprises two inductors L1 and L2 connected in series between probe 18 (depicted in FIGS. 1 and 2) and node 32. A capacitor C1 is connected, as depicted, between ground and the node formed by the connection of L1 and L2. A capacitor C2 is connected between ground and node 32.

In the illustrated embodiment, resistors R2 through R6 have a resistance of 10, 100, 1k, 10k and 100k Ohms respectively with an accuracy of 0.01%. Resistors R1 and R7 have a resistance of 10 MOhms and 1 MOhm respectively. voltage source 40 supplies less than, approximately, −12 V. Typically, voltage source 40 operates at −15 V. Inductors L1 and L2 have an inductance of 38 μH while capacitors C1 and C2 have a capacitance of 0.1 μF.

In operation, op-amp 30 of sensing circuit 22 maintains the reference voltage generated by reference voltage source 40 to probe 18. Voltmeter 44 measures the resultant current flow. The measured current is given by the relationship V/R where V is the voltage measured by volt meter 44 and R is the appropriate resistor selected in switch 46 (R2 through R6). Switch 46 allows the operator to scale the load for ease of measurement and for system flexibility. RF filter 28 ensures that current meter 44 is responsive to only DC signals from probe 18.

ELECTRON CONCENTRATION MONITOR

Generally, the electrical conductivity ($\sigma_e$) of a plasma is linearly dependent on its electron number density ($n_e$):

$$\sigma_e = \frac{n_e e^2}{m_e v_{eh}}$$

where $v_{eh}$ is the collision frequency and $m_e$ is the mass of an electron. This allows a second parameter to be used to monitor the density of a plasma for feedback purposes.

The time constant for the decay of an oscillating resonant LC circuit can be used to measure the electron density, $n_e$, using a multi-turn coil that surrounds the plasma of interest. An ideal LC circuit with no dissipation oscillates indefinitely. A lossy circuit, one with a finite non-zero resistance, has a time constant of 2 L/R, where L is the inductance of the inductor, and R is the effective resistance of the coil. RF currents circulating in an inductor surrounding a plasma induce dissipative eddy currents in the plasma. These eddy currents increase the effective resistance of such a coil. The resistance of the coil is therefore proportional to $\sigma_e$. If the additional resistance, $\Delta R$, is much larger than the intrinsic resistance of the coil, the time constant is a direct measure of the electrical conductivity of the plasma:

$$\tau_D = \frac{2L}{(\Delta R + R)} \approx \frac{2L}{\Delta R}$$

Operation of a particular resonant LC circuit can be numerically simulated by solving Maxwell's equations for the specific geometry. These calculations should be optimized for the expected electron number density, typically $10^{11}$ cm$^{-3}$. On the basis of these calculations a choice of 10 coil turns and an operating frequency of 3 MHz was made. Also, for this design the decay time is inversely proportional to the electron number density and ranges from 600 µs for $n_e=10^{10}$ cm$^{-3}$ to 6 µs for $n_e=10^{12}$ cm$^{-3}$.

One skilled in the art may adjust the particular number of coil turns and the operating frequency given the expected electron density and coil resistance in light of the foregoing description and the following design constraints. The increase in resistance ($\Delta R$) must be an order of magnitude larger than the resistance of the resonant circuit, including the leads. The time constant for decay of the oscillating LC circuit should exceed 10 µs. Time constants shorter than this are not easily measured and do not contain an adequate number of RF cycles. The operating frequency should exceed 2 MHz for most plasma conditions encountered in semiconductor processing. For operating frequencies lower than 2 MHz an increasing fraction of the total eddy current may be borne by ions. Under these conditions, the electrical conductivity can be obtained correctly, but it is no longer proportional to the electron number density alone. Thus the electron number density cannot be easily derived from the electrical conductivity.

Figure 4:
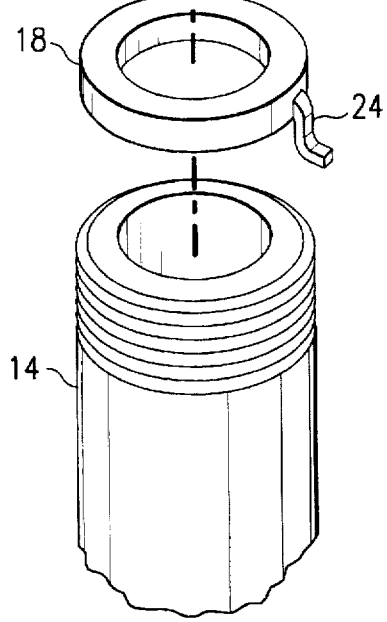
FIG. 4 depicts a partially cross sectional, partially block diagram of the disclosed electron concentration monitor.
Figure 4:
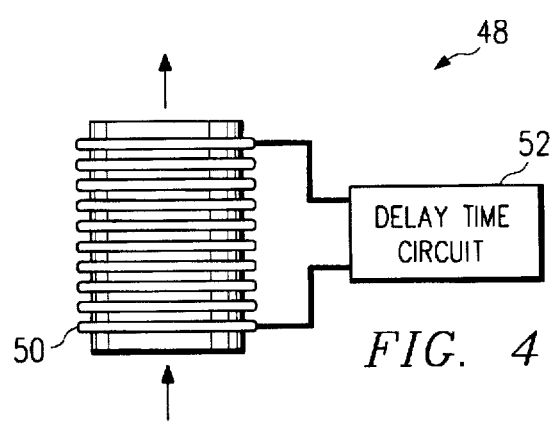

FIG. 4 depicts a partially cross-sectional, partially block diagram of the disclosed electron concentration monitor, indicated generally at 48. The monitor consists of a multi-turn coil 50 surrounding the plasma as it flows through a 1 inch diameter quartz tubular conduit 14. The measured plasma is an afterglow of a microwave produced plasma. Its direction of flow is indicated by the two arrows adjacent conduit 14. Coil 50 is electrically connected to a decay time measuring circuit 52 which measures plasma density (electron concentration) as a function of the decay time of the LC circuit. While the design discussed here has been optimized for the depicted geometry, the technique can be used for larger diameter plasma tubes as well.

Figure 5:
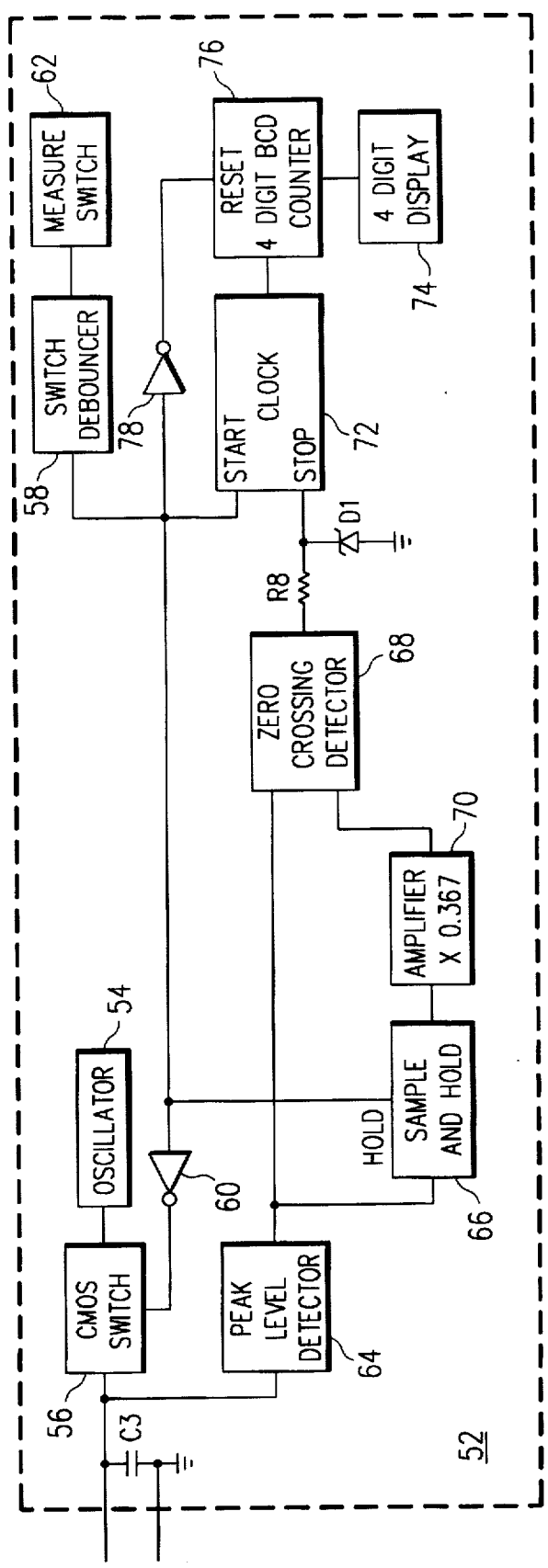
FIG. 5 depicts a partially schematic, partially block diagram of the circuit depicted in FIG. 4.

FIG. 5 depicts a partially schematic, partially block diagram of the circuit 52 depicted in FIG. 4. Inductor 50 (depicted in FIG. 4) is wired in parallel with a capacitor C3 forming the resonant part of an LC oscillator circuit. Although the capacitor is shown as having a fixed capacitance, it may be variable so that the resonant LC frequency can be adjusted to any desired value. This LC circuit is connected to an RF oscillator circuit 54 through a CMOS analog switch 56. CMOS switch 56 is controlled by the output of switch debouncer 58 inverted by inverter 60. Switch debouncer 58 debounces the output from a measure switch 62. The amplitude of the output signal from the LC circuit is monitored by a peak level detector 64. The output of peak level detector 64 is fed to a sample and hold circuit 66 and to a zero crossing detector 68. Sample and hold circuit 66 is triggered by the output from measure switch 62. Zero crossing detector 68 also has as an input, the output of an amplifier 70. Amplifier 70 has as its input the output of sample and hold circuit 66. Amplifier 70 reduces its input by approximately 63%.

Decay time circuit 52 also comprises a clock 72 which drives a display circuit 74 through a counter circuit 76. Clock 72 is started by the output of switch debouncer 58 and stopped by the output of zero crossing detector 68 fed through a resistor R8. A Zener diode D1 is connected between resistor R8 and ground as depicted. Counter circuit 76 is reset by the output of switch debouncer 58 inverted by inverter 78.

In operation, oscillator 54 is powered, CMOS switch 56 is closed and the LC circuit resonates at the operating frequency of oscillator 54. Here, oscillator 54 operates at 3 MHz. The operator then initiates a measurement by closing measure switch 62. This triggers three actions:

1. The output of switch 62 is first debounced by switch debouncer 58 so that the effective switch closure occurs in less than 100 ns. The debounced signal is inverted by inverter 60. This opens analog CMOS switch 56 thereby isolating the LC circuit from oscillator 54. The amplitude of the resonating signal in the LC circuit will then begin to decay. The time to decay will depend upon the electron number of the plasma surrounded by the inductor as described above.
2. The initial amplitude (driven by oscillator 54) of the RF oscillation is recorded by sample and hold circuit 66.
3. Clock 72 is started, and counter 76 begins to count.

The peak amplitude of oscillation of the LC circuit is continuously monitored by peak level detector 64. The time constant of the detector is adjusted so that its output traces the envelope of the oscillation. When the amplitude decreases to 37% of its initial value, the zero crossing detector is triggered. This signal stops clock 72. The count is displayed on the display 74. This count is a direct measure of the decay time in units of 0.1 µs if counter 76 is a binary coded decimal ("BCD") counter and clock 72 is a 10 MHz clock as they are in the depicted embodiment. When switch 62 is opened, the counter is reset to zero, and CMOS switch 56 is closed.

Although the present invention and its advantages have been described in detail, it should be understood that various changes, substitutions and alterations can be made herein without departing from the spirit and scope of the invention as defined by the appended claims.

What is claimed is:

1. A system for measuring the plasma density of an afterglow of a microwave induced plasma, comprising:
   a processing chamber;
   a microwave induced plasma source;
   a non-conductive conduit for flowing the plasma from the source into the chamber;

a multi-turn coil surrounding the conduit;

a capacitor coupled with the coil to form a resonant LC circuit with a time constant;

an oscillator circuit coupled to drive the LC circuit into oscillation; and a decay time measuring circuit coupled to the LC circuit for measuring the decay time of the oscillated LC circuit;

the coil, capacitor, conduit and oscillator circuit being relatively dimensioned, configured and positioned for inducing currents in the plasma afterglow to vary the decay time of the LC circuit proportional to the electrical conductivity of the plasma.

2. The system of claim 1, wherein the resonant LC circuit has an intrinsic resistance; and the coil, capacitor, conduit and oscillator circuit are relatively dimensioned, configured and adapted for inducing eddy currents in the plasma that increase the effective resistance of the coil by an order of magnitude larger than the intrinsic resistance of the resonant LC circuit.

3. The system of claim 1, wherein the resonant LC circuit has a decay time that exceeds 10 µs.

4. The system of claim 1, wherein the oscillator circuit is an RF oscillator circuit dimensioned and configured to drive the LC circuit into oscillation at an operating frequency that exceeds 2 MHz.

5. The system of claim 1, wherein the conduit is a tubular quartz conduit.

6. The system of claim 5, wherein the conduit is a one-inch diameter quartz conduit and the coil has 10 turns.

7. The system of claim 1, wherein the RF oscillator circuit includes an oscillator, a CMOS switch for selectively isolating the oscillator from the LC circuit, a measure switch for initiating a measurement, and a switch debouncer coupled to debounce the output of the measure switch for controlling operation of the CMOS switch.

8. The system of claim 7, wherein the switch debouncer is dimensioned and configured to debounce the output of the measure switch to provide an effective switch closure time of less than 100 ns.

9. The system of claim 1, wherein the RF oscillator circuit includes an oscillator, and a switch circuit for selectively isolating the oscillator from the LC circuit; and the decay time measuring circuit includes a peak level detector circuit coupled to the LC circuit for monitoring the peak voltage amplitude of the oscillated LC circuit; a sample and hold circuit coupled to the peak level detector and the switch circuit for capturing the initial voltage amplitude of the LC circuit; an amplifier coupled to the sample and hold circuit for providing a measurement ending reference voltage by reduced amplification of the captured initial voltage amplitude; a zero crossing detector coupled to the peak level detector and amplifier for determining when the peak voltage amplitude monitored by the peak level detector has reached the measurement ending reference voltage; and a clock circuit coupled to be started by the switch circuit and stopped by the zero crossing detector, for determining the decay time.

10. The system of claim 9, wherein the oscillator is dimensioned and configured to operate at 3 MHz.

11. The system of claim 10, wherein the clock circuit comprises a clock, a display and a counter, relatively coupled so that the clock is started by the switch circuit, stopped by the zero crossing detector, and drives the display through the counter.

12. The system of claim 11, wherein the clock is a 10 MHz clock, and the counter is a binary coded decimal counter.

13. The system of claim 12, wherein the amplifier is dimensioned and configured to provide a reference voltage equal to 37% of the captured initial voltage amplitude.

14. A system for measuring the plasma density of an afterglow of a microwave induced plasma, comprising:

a processing chamber;

a microwave induced plasma source located outside the chamber;

a non-conductive tubular conduit for flowing the plasma from the source into the chamber;

a multi-turn coil surrounding the conduit;

a capacitor coupled in parallel with the coil to form a resonant LC circuit with a time constant;

an RF oscillator circuit coupled to drive the LC circuit into oscillation; the RF oscillator circuit including an oscillator and a switch circuit for selectively isolating the oscillator from the LC circuit for initiating a measurement; and a decay time measuring circuit coupled to the LC circuit for measuring the decay time of the oscillated LC circuit; the decay time measuring circuit including a peak level detector circuit coupled to the LC circuit for monitoring the peak voltage amplitude of the oscillated LC circuit; a sample and hold circuit coupled to the peak level detector and the switch circuit for capturing the initial voltage amplitude of the LC circuit; a measurement ending reference voltage source; a zero crossing detector coupled to the peak level detector and the ending reference voltage source for determining when the peak voltage amplitude monitored by the peak level detector has reached the measurement ending reference voltage; and a clock circuit coupled to be started by the switch circuit and stopped by the zero crossing detector, for determining the decay time.

15. The system of claim 14, wherein the coil, capacitor, conduit and RF oscillator circuit being relatively dimensioned, configured and positioned to provide a time constant greater than 10 µs and an operating frequency greater than 2 MHz.

16. The system of claim 15, wherein the resonant LC circuit has an intrinsic resistance; and the coil, capacitor, conduit and RF oscillator circuit are relatively dimensioned, configured and adapted for inducing eddy currents in the plasma that increase the effective resistance of the coil by an order of magnitude larger than the intrinsic resistance of the resonant LC circuit.

17. A system for measuring the plasma density of an afterglow of a microwave induced plasma, comprising:

a processing chamber;

a microwave induced plasma source located outside the chamber;

a non-conductive conduit for flowing the plasma from the source into the chamber;

a multi-turn coil surrounding the conduit;

a capacitor coupled in parallel with the coil to form a resonant LC circuit with a time constant;

an RF oscillator circuit coupled to drive the LC circuit into oscillation; the RF oscillator circuit including an oscillator and a switch circuit; the switch circuit comprising a first switch for selectively isolating the oscillator from the LC circuit, a second switch for initiating a measurement, and a switch debouncer coupling the second switch for control of the first switch; and a decay time measuring circuit coupled to the LC circuit for measuring the decay time of the oscillated LC circuit; the decay time measuring circuit including a peak level detector circuit coupled to the LC circuit for monitoring the peak voltage amplitude of the oscillating LC circuit; a sample and hold circuit coupled to the peak level detector and the switch circuit for capturing the initial voltage amplitude of the LC circuit; an amplifier coupled to the sample and hold circuit for providing a measurement ending reference voltage by reduced amplification of the captured initial voltage amplitude; a zero crossing detector coupled to the peak level detector and amplifier for determining when the peak voltage amplitude monitored by the peak level detector has reached the measurement ending reference voltage; and a clock circuit coupled to be started by the switch circuit and stopped by the zero crossing detector, for measuring the decay time.

18. The system of claim 17, wherein the sample and hold circuit is coupled to the switch debouncer, for capturing the initial voltage amplitude in response to the debounced effect of activation of the second switch.

19. The system of claim 17, wherein the clock circuit comprises a 10 MHz clock coupled to be started by the switch debouncer and stopped by the zero crossing detector; and a binary coded decimal counter coupled to be driven by the clock and reset by the switch debouncer.

20. The system of claim 17, wherein the resonant LC circuit has a decay time that exceeds 10 µs; and wherein the oscillator has an operating frequency greater than 2 MHz.

* * * * *